United States Patent
Farkas et al.

Patent Number: 5,477,853
Date of Patent: Dec. 26, 1995

[54] TEMPERATURE COMPENSATION METHOD AND APPARATUS FOR SPECTROSCOPIC DEVICES

[75] Inventors: Richard A. Farkas, Bloomfield Hills; Gary D. Lewis, St. Clair Shores, both of Mich.

[73] Assignee: Somanetics Corporation, Troy, Mich.

[21] Appl. No.: 983,817

[22] Filed: Dec. 1, 1992

[51] Int. Cl.$^6$ .................................................. A61B 5/00
[52] U.S. Cl. ................................................... 128/633
[58] Field of Search ...................... 356/326; 372/31, 372/32; 128/632, 633, 664, 665; 604/31

[56] References Cited

U.S. PATENT DOCUMENTS

| | | | |
|---|---|---|---|
| 4,181,610 | 1/1980 | Shintani et al. | 604/31 X |
| 4,364,008 | 12/1982 | Jacques | 128/632 |
| 4,549,073 | 10/1985 | Tamura et al. | 219/497 |
| 4,570,638 | 2/1986 | Stoddart et al. | 128/665 |
| 4,723,554 | 2/1988 | Oman et al. | 128/633 X |
| 4,763,655 | 8/1988 | Wirtzfeld et al. | 128/633 X |
| 4,768,516 | 9/1988 | Stoddard et al. | 128/665 |
| 4,770,179 | 9/1988 | New, Jr. et al. | 128/633 |
| 4,807,630 | 2/1989 | Malinouskas | 128/633 |
| 4,817,623 | 4/1989 | Stoddart et al. | 128/665 |
| 4,892,101 | 1/1990 | Cheung et al. | 128/633 |
| 4,913,150 | 4/1990 | Cheung et al. | 128/664 X |
| 4,926,867 | 5/1990 | Kanda et al. | 128/664 X |
| 5,081,998 | 1/1992 | Yelderman et al. | 128/664 X |
| 5,139,025 | 8/1992 | Lewis et al. | 128/665 |
| 5,150,969 | 9/1992 | Goldberg et al. | 128/664 X |
| 5,188,108 | 2/1993 | Secker | 128/633 |
| 5,204,532 | 4/1993 | Rosenthal | 128/633 X |
| 5,291,884 | 3/1994 | Heinemann et al. | 128/633 |

*Primary Examiner*—Lee S. Cohen
*Assistant Examiner*—Samuel Gilbert
*Attorney, Agent, or Firm*—Price, Heneveld, Cooper, DeWitt & Litton

[57] ABSTRACT

An apparatus and method which detects temperature variations of an LED used with spectroscopic devices. The apparatus and method uses a source to supply a signal to the LED. A detector coupled to the LED detects a signal at the LED. A controller is coupled to the detector to determine variations in operating characteristics of the LED resulting from changes in temperature.

21 Claims, 3 Drawing Sheets

TEMPERATURE COMPENSATION METHOD AND APPARATUS FOR SPECTROSCOPIC DEVICES

CROSS REFERENCE TO RELATED APPLICATIONS

This patent application is related to copending U.S. patent application Ser. No. 07/711,452, filed 6 Jun. 1991 now U.S. Pat. No. 5,217,013, and copending U.S. application Ser. No. 07/711,147, filed 6 Jun. 1991, which is a continuation-in-part of U.S. application Ser. No. 07/329,945, filed 29 Mar. 1989, now U.S. Pat. No. 5,139,025, which is related to patents U.S. Pat. Nos. 4,768,516; 4,817,623; 4,570,638, the disclosures of each of these applications and patents incorporated herein by reference thereto.

TECHNICAL FIELD

This invention relates generally to spectroscopic methods and apparatus of the type using a light emitting diode (LED). More particularly, this invention relates to a method and apparatus which compensates for temperature variations of an LED used in a spectroscopic device.

BACKGROUND OF THE INVENTION

Spectroscopy has long been utilized as a valuable investigative tool in various scientific fields. In particular, biological and medical research is conducted based on spectroscopic equipment which takes advantage of the underlying principles of selected wavelengths, such as the near infrared range. Examples of spectroscopic devices and applications thereof are disclosed and described in the patents and patent applications incorporated hereinabove by reference. Those skilled in the art will recognize other spectroscopic devices in applications in which the invention may be advantageously utilized.

It is highly desirable to employ LEDs in spectroscopic equipment. LEDs are relatively inexpensive to manufacture and are small in size. However, putting LEDs to use in the exacting environment of spectroscopic devices has presented significant difficulties which have heretofore not been sufficiently overcome.

Operating characteristics of diodes vary from unit to unit. For example, the wavelength of light emitted from different diodes are not identical. Such variations in wavelength are detrimental to the successful employment of LEDs in equipment for monitoring or testing biological substances. For example, spectroscopic devices used to analyze human bone, skin, or tissue, must have a light source emission within a known, narrow bandwidth to operate accurately. Accordingly, spectroscopic devices employing LEDs are carefully calibrated when the LED is installed.

One attempt at accounting for variations in emission frequencies of different LEDs used in spectroscopic devices uses an encoding component, such as a resistor of known resistance, selected to correspond to the measured wavelengths of light emitted from an associated LED. A detector which is used with the LED may identify the wavelength of light emitted by a particular LED by looking at its associated resistor.

Even if calibration and wavelength identification allow wavelength variations of diodes to be identified and compensated for at the calibration temperature, these techniques do not compensate for environmental changes, such as ambient temperature variations, of the LED. For example, in the novel oxymeter disclosed in U.S. patent application Ser. No. 07/711,147, an LED is placed in the proximity of a brain during surgery to monitor the oxygen level of the brain. In some operations, the brain is chilled during surgery. Because a thermal coupling exists between the sensor and the patient when the sensor is placed in the proximity of the chilled brain, the temperature of the diode junction will drop. With this drop in junction temperature, the intensity and wavelength of the LED emission will vary. This variation in wavelength and intensity causes substantial errors in the oxymeter measurements.

It is known to provide a resistive heating element to maintain a desired temperature under varying ambient conditions. However, for such a heating element to raise the temperature of an LED used in a spectroscopic sensor, the temperature externally of the sensor will also be raised. As a result, the temperature of the biological matter adjacent the sensor will also rise. Further, a substantial amount of circuitry and connectors would have to be used to implement such a heating element in a sensor for a spectroscope. Accordingly, it remains highly desirable to compensate for temperature variations occurring at the junction of an LED which is used in spectroscopic devices.

SUMMARY OF THE INVENTION

The apparatus according to the present invention effects a novel method of compensating for temperature variations of an LED used in spectroscopic devices to eliminate errors in measurements made using such devices. More broadly considered, the apparatus and method according to the invention provide a novel method of adapting equipment to accommodate for variations in wavelengths and intensity of LED emissions wherein such emission wavelengths and intensity are critical to the accuracy of the equipment.

According to one aspect of the invention, a temperature compensation apparatus includes a current source supplying current to the LED. A voltage detector is connected to the LED to sense the forward voltage of the LED and output a signal proportional thereto. A controller connected to the voltage detector is responsive to the output signal for detecting variations in the emission characteristics of the LED.

According to another aspect of the invention, a method of compensating for temperature variations of an LED includes applying a reference current to the LED. A resultant LED signal is detected responsive to the reference current. The resultant signal is compared to a reference parameter to determine variations in the emission characteristics of the LED. Responsive to the determined variations, a sensed signal is adjusted to compensate for errors resulting from the variations in emission characteristics.

According to yet another aspect of the invention, the resultant LED signal is detected immediately following the cessation of a current pulse used for spectroscopic analysis. Preferably, a small current is supplied to the LED between pulses which is used for detecting variations in emission characteristics of the LED.

The invention allows an LED to be utilized in temperature variant conditions without detrimentally effecting the accuracy of the results obtained using such LED. The system is particularly advantageous where the wavelength and intensity of light emitted by an LED are critical to the accuracy of equipment using such LED. The temperature compensation circuit is relatively inexpensive to implement and provides a significant improvement in test result accuracy.

The foregoing major objectives, advantages and considerations of the invention, together with and including others, will become more apparent following consideration of the following specification, particularly taken in connection with the appended drawings, briefly described hereinafter. Once again it is pointed out that the apparatus and methodology described hereinafter constitutes merely a preferred embodiment of the underlying invention, and does not specifically address other and further aspects thereof which will be further appreciated by those skilled in the art after consideration of the overall disclosure herein.

DETAILED DESCRIPTION OF THE PREFERRED EMBODIMENT

Figure 1:
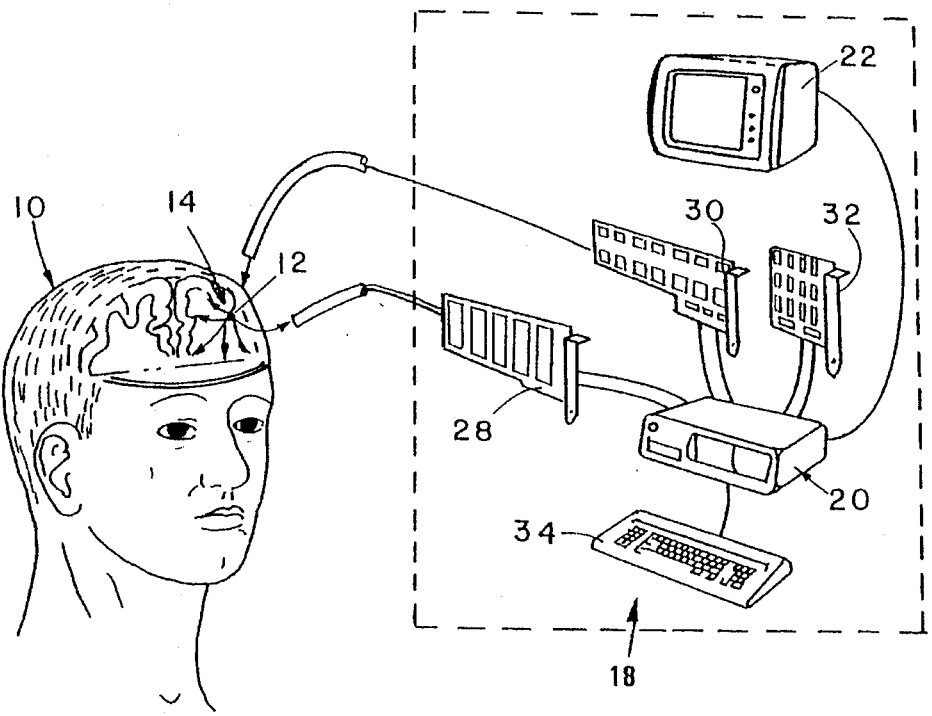
FIG. 1 is a pictorial schematic representation simplistically illustrating one basic application and utilization of apparatus according to the invention.

A temperature compensation method and apparatus according to the illustrated embodiment of the invention is adapted for use in various types of spectroscopic devices. Detectors are used which detect the emission of an LED in a variety of different spectroscopic implementations. An example of one such spectroscopic device is the optical cerebral oximeter pictorially and schematically shown in FIG. 1. It will be recognized that although the invention is illustrated in an optical cerebral oximeter, the temperature compensation method and apparatus according to the invention can be advantageously utilized in other spectroscopic devices. Hence, it will be recognized by those of ordinary skill in the art that the invention may be used in any environment where the wavelength and intensity of the light emitted by an LED is critical. However, the invention is particular advantageous when utilized with spectrophotometric equipment employing LEDs. Accordingly, as used herein, "spectroscopic devices" are not limited to the specific cerebral oximeter in which the invention is illustrated herein.

As shown in the drawings, the illustrated spectroscopic device is used with a human subject 10. The device includes a sensor means 12 for applying and receiving selected light spectra to a particular region 14 of the brain. The light spectra is applied and received by sensor 12 responsive to signals passing through conductors 16 which may be optical and/or electrical in nature. Spectrophotometer 18 is connected to the other end of conductor 16 opposite sensor 12. Somewhat more particularly, spectrophotometric unit 18 includes a small digital computer 20 having a monitor 22 on which information is presented to a user. Sensor 12 applies selected light wavelengths utilizing selected LEDs. Computer 20 generally includes an A/D converter section 28, control circuitry 30 (depicted as a circuit board configured to mount in expansion slots of computers 20), together with requisite computer memory 32 and operator control in the form of keyboard 34. The illustrated spectrophotometer is described in greater detail in the above referenced copending U.S. application Ser. No. 07/711,457, incorporated hereinabove by reference. Accordingly, the aspects of spectrophotometer apparatus 18 described in the parent application will not be described in greater detail hereinafter.

Figure 4:
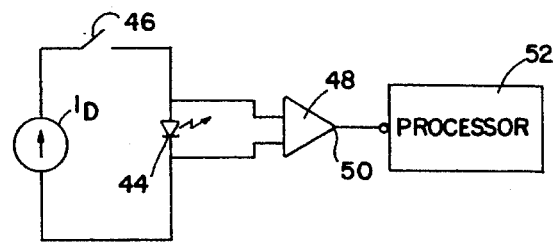
FIG. 4 is a schematic representation of a circuit according to the invention.
Figure 5:
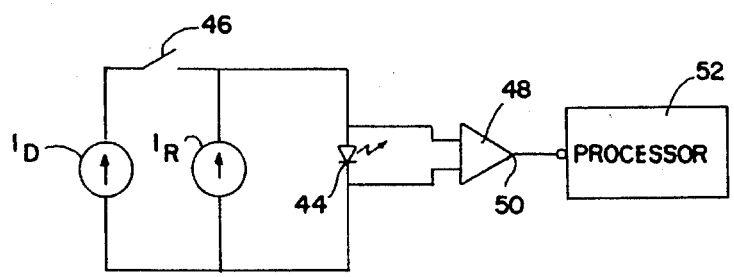
FIG. 5 is a schematic representation of an alternate embodiment of the circuit of FIG. 4.
Figure 6:
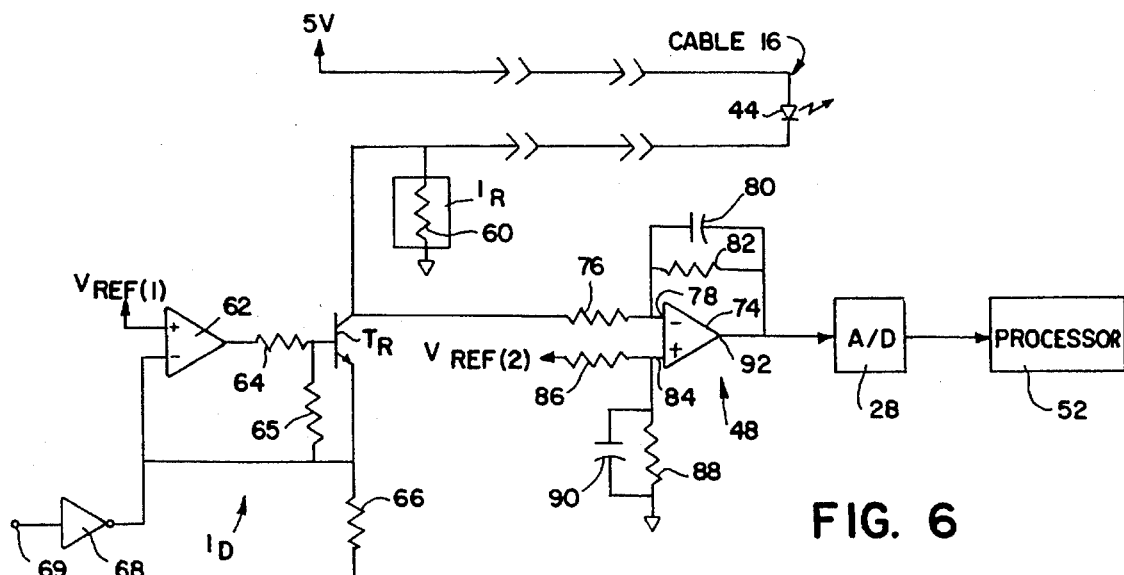
FIG. 6 is a circuit diagram of the embodiment illustrated schematically in FIG. 5.

Sensor assembly 12 may as a general matter be in accordance with the above referenced copending U.S. application Ser. No. 07/711,452, incorporated hereinabove by reference thereto. Generally, the sensor assembly 12 is elongated in shape and includes a somewhat flexible support 36 which carries a light source 38 and near and far receivers 40, 42, all arranged in a longitudinal array. Source 38 preferably comprises a pair of separate, commonly mounted LEDs and receivers 40 and 42 are comprised of photo diodes. One LED 44 of source 38 is illustrated in FIGS. 4–6. Sensor assembly 12 is relatively small and compact, lightweight and thin. The electrical components of sensor assembly 12 are coupled to the spectrophotometer 18 by electrical conductor 16 carried within an insulator outer sheath 17. Again, it will be recognized that sensor assembly 12 is provided for illustrative purposes, and the invention described herein will find application with other spectroscopic sensors using LEDs.

Regardless of the particular spectroscopic device, the apparatus and method according to the invention detects and compensates for temperature variations at the junction of an LED 44. The apparatus includes a current source $I_D$ (FIG. 3) connected to LED 44 through a switch 46. Current source $I_D$ in the illustrated embodiment provides a pulse of current to LED 44 when switch 46 is closed. LED 44 emits light in the near infrared range responsive to the current pulse from source $I_D$. Receivers 40, 42 (FIG. 2) are responsive to the light from LED 44 (FIG. 3) to output signals which are used by spectrophotometer 18 to determine the $O_2$ level of the brain as described in copending U.S. application Ser. No. 07/711,147. A detector 48 is connected across LED 44 to detect the junction voltage thereof when current from source $I_D$ is supplied to the LED. The output 50 of detector 48 is connected to a processor means 52. Processor 52 is provided in spectrophotometer 18.

Figure 8:
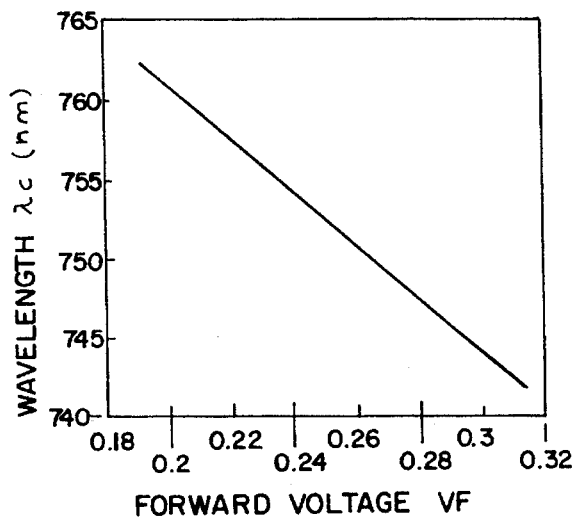
FIG. 8 is a graphical representation illustrating wavelength versus forward voltage for an LED.
Figure 9:
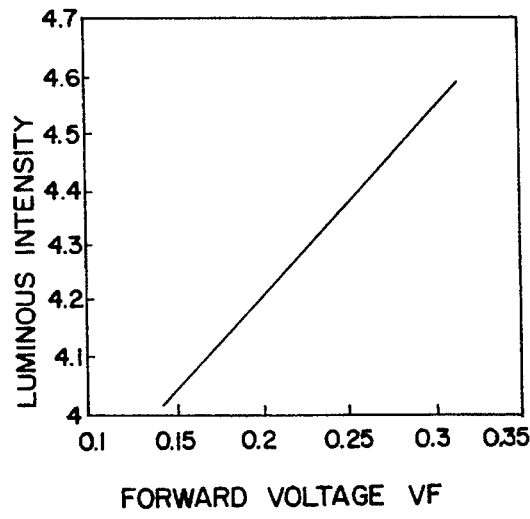
FIG. 9 is a graphical representation illustrating radiant intensity versus forward voltage for an LED.
Figure 10:
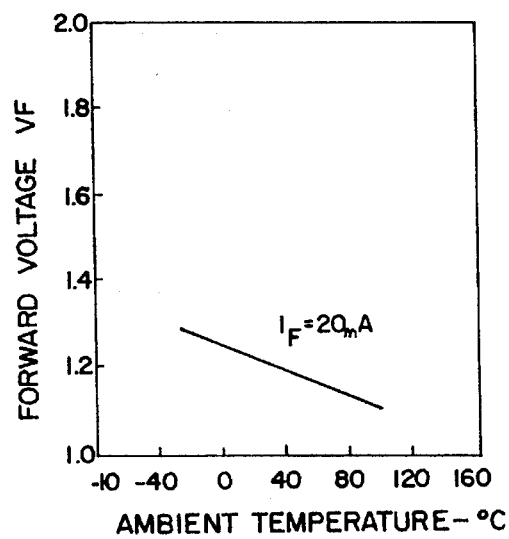
FIG. 10 is a graphical representation illustrating the forward voltage versus ambient temperature variations for a fixed forward current to an LED.
Figure 11:
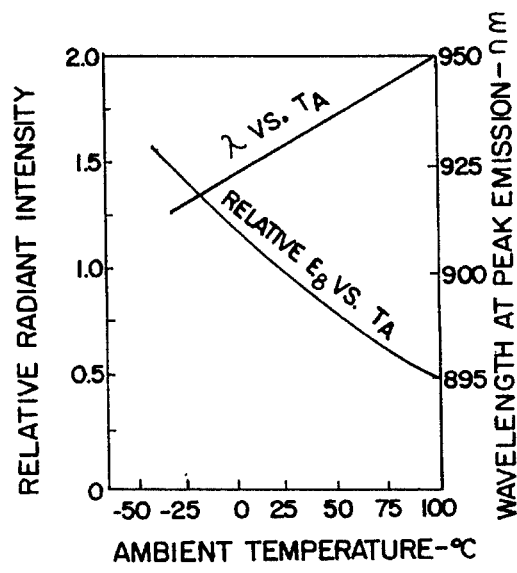
FIG. 11 is a graphical representation illustrating the center frequency versus ambient temperature and the relative radiant intensity versus ambient temperature for an LED.

Processor 52 stores parameters and relationships of the LED as described hereinbelow. Through experimentation, Applicant determined the relationship between the center wavelength (or peak emission wavelength) of LEDs as a function of forward voltage (FIG. 8), and luminous intensity as a function of forward voltage (FIG. 9). As illustrated in FIG. 8, the center wavelength ($\lambda_c$) of an LED emission decreases in a substantially linear manner with increasing forward voltage VF. The relative intensity of the light emission of LEDs (FIG. 9) increases with increasing forward voltage VF, also in a substantially linear manner. Applicant's findings are supported by general characteristics of LEDs. As represented by FIG. 10, for a fixed current (e.g., 20 mA), as temperature increases, forward voltage VF decreases. Additionally, radiant intensity decreases with increasing temperature (FIG. 11), whereas the peak emission wavelength increases with increasing ambient temperature. These characteristics of LEDs represented by FIGS. 8 and 9 were found to be repeatable from LED to LED. Accordingly, expected variations in wavelength and intensity of LED emissions corresponding to changes in forward voltage VF, as represented by FIGS. 8 and 9, are stored in processor 52. It will be recognized that processor 52 may store wavelength vs. forward voltage characteristics, and intensity vs. forward voltage characteristics, for the specific LED 44 with which it is used. However, the preferred embodiment uses general characteristics determined for LEDs of the type utilized in the spectroscopic equipment stored in processor 52.

Calibration of processor 52, and thus spectrophotometer 18, for sensor assembly 12 requires additional considerations. At the time of installation of LED 44 (e.g., when sensor 12 is connected to spectrophotometer equipment 18), the ambient temperature $T_O$, the forward voltage $VF_O$ of LED 44 responsive to current $I_D$ at temperature $T_O$, the center frequency $\lambda_{co}$ of the LED 44 emission generated in response to current $I_D$ at temperature $T_O$, and the intensity $E_O$ of the LED 44 emission generated in response to current $I_D$ at temperature $T_O$, are stored in processor 52. These stored values are reference values which are utilized by the processor during operation of the circuit. The variations in the intensity and the center wavelength of the light emitted by LED 44 for incremental changes in forward voltage, represented generally by FIGS. 8 and 9, are also stored. For example, processor 52 may include a look-up table containing values of the wavelength change and intensity change for each 1 millivolt shift in forward voltage VF.

In operation, when a current pulse is input to LED 44 from source $I_D$, LED 44 emits light which is detected by receivers 40, 42. Simultaneously therewith, detector 48 measures the forward voltage on LED 44. Responsive thereto, detector 48 outputs a signal to processor 52.

Processor 52 compares the detected forward voltage output from detector 50 with the stored reference forward voltage $VF_O$. The difference in voltage between voltage $VF_O$ and the detected voltage correspond to a known shift (FIGS. 8 and 9) in the intensity and center wavelength of the light output by LED 44. The shift in intensity and center wavelength corresponding to the detected voltage difference is then added to, or subtracted from, the stored reference wavelength $\lambda_{co}$ and intensity $E_O$ values to determine the present wavelength and intensity values. In this manner, the changes in wavelength and intensity of the LED radiant energy resulting from temperature variations, or other changes in environmental or LED conditions, are determined at the time of pulse transmission.

The signal detected by receivers 40, 42 are processed by spectrophotometer 18 as more fully described in copending U.S. application Ser. No. 07/711,147. However, those skilled in the art will recognize that the determination of the $O_2$ level in spectrophotometer 18 is dependent upon the intensity and wavelength of the radiant energy emitted by LED 44. These intensity and wavelength variations are then factored into the determination of $O_2$ levels by adjusting the wavelength and intensity variables for reductions and increases in the intensity of the LED emission as well as increases and reductions in the wavelength of the LED emission. Thus, the intensity and wavelength information detected by processor 52 is used to adjust the spectrometer 18 to eliminate errors resulting from calculations of the $O_2$ levels based upon incorrect intensity and wavelength values.

Figure 2:
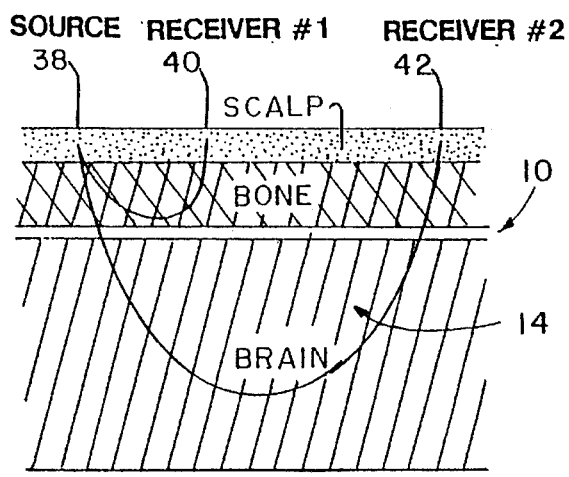
FIG. 2 is a schematic representation depicting the regional examination of a head and brain in the application and utilization according to FIG. 1, wherein the invention may be advantageously utilized.
Figure 3:
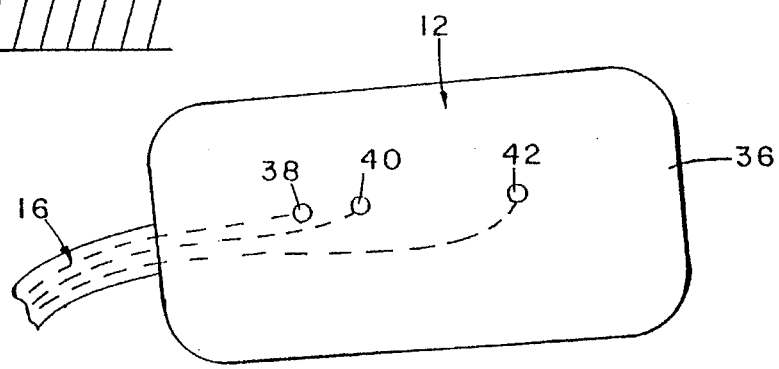
FIG. 3 is a pictorial side view representation of an optical sensor used in the environment of FIGS. 1 and 2, with which the invention may be used.

An alternate embodiment of the temperature compensation apparatus is disclosed in FIG. 5. The embodiment of FIG. 5 differs from the embodiment of FIG. 4 in that it further includes a current source $I_R$. Current source $I_R$ supplies a small current, or trickle current, to LED 44. Constant current source $I_D$ is significantly larger than constant current source $I_R$. Current source $I_D$ is large enough that receivers 40, 42 detect light emitted by LED 44 which passes through human subject 10 as illustrated in FIG. 2. Current source $I_R$ is significantly smaller in magnitude, such that LED 44 does not emit sufficient radiant energy responsive to current $I_R$ to pass radiant energy to detectors 40, 42. In one particularly advantageous implementation, source $I_D$ generates a current of 200 milliamps and source $I_R$ generates a current of 1 milliamp.

A specific implementation of the schematic representation of FIG. 5 is disclosed in FIG. 6. The anode of LED 44 is connected to a 5 volt source through cable 16. Constant current source $I_R$ is provided by resistor 60 connected between the cathode of LED 44 and circuit ground. Current source $I_D$ includes a transistor $T_R$, and amplifier 62, resistors 64 and 65 and an emitter resistor 66. Pulses are input to inverter 68 as control signals. These control signals control the generation of the current pulses by current source $I_D$. The control signals are applied via inverter 68 to amplifier 62, which in turn applies the base drive current to transistor $T_R$. Transistor $T_R$ draws current from the 5 volt source through LED 44 when the transistor is in a conductive state.

Detector 50 is connected to the junction of the collector of NPN transistor $T_R$ and the cathode of LED 44. Detector 50 includes a differential amplifier 74 and associated resistors and capacitors. An input resistor 76 is connected between the inverting input 78 of amplifier 74 and the cathode of LED 44. Negative feedback is provided by a capacitor 80 and a resistor 82 connected in parallel. The non-inverting input 84 of amplifier 74 is connected to a junction of a resistor 86 and a parallel connection of a resistor 88 and a capacitor 90. The output 92 of amplifier 74 is connected to the input of A/D converter 28. The output of A/D converter 28 is in turn connected to processor 52.

The operation of the alternate embodiment is substantially identical to the operation of the embodiment of FIG. 4. The difference in operation will now be described with reference to FIG. 7. Current pulses from current source $I_D$ are superimposed on current $I_R$ when switch 46 is closed. The sampling time $T_M$ of the detector circuit 48 follows immediately after the transmission of each current pulse $I_D$. Applicants have discovered that by measuring immediately after the $I_D$ current pulse, and by using a significantly smaller testing current, the extraneous $I_D$ voltage drop across the junction of LED 44 is significantly reduced. Because measurements of the LED forward voltage are based on current $I_R$, the reference parameters $VF_O$, $\lambda_{co}$, and $E_O$ are generated from current $I_R$. Processor 52 otherwise operates in the same manner as described above with reference to FIG. 3. Accordingly, its operation will not be described again.

Figure 7:
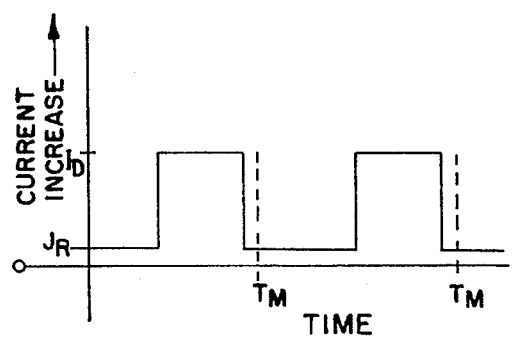
FIG. 7 is a graphical representation illustrating timing considerations in the circuit of FIG. 6.

The alternate embodiment illustrated in FIGS. 5 through 7 is particularly advantageous where current source $I_D$ is remote from LED 44. For example, current source $I_D$ may be connected through several long cables. In such a situation, the voltage drop measured by detector 48 includes the voltage drop across the resistance of the cable, the cable connectors, and the sensor circuit connectors. By injecting the small steady state current $I_R$, which is not pulsed, the LED voltage measurement can be taken without applying the large pulse current. Accordingly, the large impressed voltage drop caused by $I_D$ passing through these impedances and the diode does not effect the accuracy of the measurement of the intensity and peak wavelength of the LED. Thus, surprisingly, by testing with the trickle current following the pulse, the LED parameter measurements are significantly improved.

It can be seen that a method and apparatus for compensating for temperature variations of an LED are disclosed. The circuit requires a relatively small amount of additional circuitry, and thus is inexpensive to implement. The circuit is particularly advantageous for measuring variations in LED characteristics in those environments where the wavelength and intensity of emissions of an LED are critical.

In the foregoing description, it will be readily perceived by those skilled in the art that modifications may be made to the invention without departing from the concepts disclosed herein. Such modifications are to considered as included in the following claims, unless these claims by their language expressly state otherwise.

The embodiments of the invention in which an exclusive property or privilege is claimed are defined as follows:

1. Apparatus for determining variations in operating characteristics of a spectroscopic device, comprising:

an LED;

a current generator having an output connected to the LED to apply a current thereto;

a voltage detector having at least one input and at least one output, and circuitry connecting said at least one input mid output of said voltage detector across said LED, said voltage detector including means to detect the voltage across said LED when said current is applied to said LED and provide a characteristic signal at said at least one output which has a predetermined relationship to said detected voltage and which characterizes the particular operation of said LED; and a processor coupled to said at least one output of said detector to receive said characteristic signal provided by said detector, said processor including means to provide an output in response to said characteristic signal which is representative of variations in the operating characteristics of said LED resulting from temperature changes of said LED.

2. The apparatus as defined in claim 1 wherein said current generator includes means for generating intermittent pulses of current and a small trickle current between said intermittent pulses, said pulses being substantially larger in magnitude than said trickle current.

3. The apparatus as defined in claim 2 wherein said processor includes means for determining variations in operating characteristics of said LED responsive to said trickle current when said intermittent pulses of current are not being generated.

4. Apparatus for determining variations in operating characteristics of a spectroscopic device, comprising:

an LED;

a current generator having a current output connected to said LED to apply said current output thereto;

a voltage detector, said voltage detector having at least one input and at least one output, means for connecting said at least one input of said voltage detector to at least one terminal of said LED such that, said voltage detector detects a voltage level at said at least one terminal of said LED when said current output is applied to said LED and provides a characteristic signal at said at least one output which has a predetermined relationship to said detected voltage level;

a processor coupled to said at least one output of said detector to receive said characteristic signal provided by said voltage detector, said processor including means for determining variations in operating characteristics of said LED from said characteristic signal including variations which result from temperature changes of said LED; and said current generator including a constant current source.

5. Apparatus for determining variations in operating characteristics of a spectroscopic device, comprising:

an LED;

a current generator, said current generator supplying a current at an output thereof, said output connected to said LED to apply said current thereto;

a voltage detector, said voltage detector having at least one input and at least one output, said at least one input of said voltage detector connected to at least one terminal of said LED such that said voltage detector detects a voltage level at said at least one terminal of said LED when said current is applied to said LED and provides a characteristic signal at said at least one output having a predetermined relationship to said detected voltage level;

a processor coupled to said at least one output of said detector to receive said characteristic signal provided by said detector, said processor including means to determine from said characteristic signal variations in operating characteristics of said LED including variations which result from temperature changes of said LED;

said current generator including means for generating intermittent pulses of current and a small trickle current between said intermittent pulses, said pulses being substantially larger in magnitude than said trickle current;

said processor including means for determining variations in operating characteristics of said LED responsive to said trickle current when said intermittent pulses of current are not being generated; and said detecting means being responsive to said characteristic signal substantially immediately following a downward transition of each said intermittent pulse to detect said variations in operating characteristics of said LED.

6. Apparatus for determining variations in operating characteristics of a spectroscopic device, comprising:

an LED;

a current generator having a current output connected to said LED to apply said current output thereto;

a voltage detector, said voltage detector having at least one input and at least one output, means connecting said at least one input of said voltage detector to at least one terminal of said LED, said voltage detector including means to detect a voltage level at said at least one terminal of said LED when said current output is applied to said LED and to provide a characteristic signal at said at least one output which has a predetermined relationship to said detected voltage level;

a processor coupled to said at least one output of said detector to receive said characteristic signal provided by said detector, said processor including means to determine from said characteristic signal variations in operating characteristics of said LED including variations which result from temperature changes of said LED; and said LED having an associated reference voltage parameter, said processor including memory, and said reference voltage parameter being stored in said processor memory.

7. The apparatus as defined in claim 6 wherein said processor includes means for determining said variations in operating characteristics of said LED from said reference voltage parameter and said characteristic signal.

8. The apparatus as defined in claim 7, where said processor includes means to determine a wavelength variation in the light emitted from said LED on the basis of said reference voltage parameter and said characteristic signal.

9. The apparatus as defined in claim 7, wherein said processor includes means to determine a variation in intensity of the light emitted from said LED on the basis of said reference voltage parameter and said characteristic signal.

10. A spectroscope, comprising:

and LED having first and second terminals;

a photodetector positioned to receive light emitted by said LED, said photodetector having outputs providing output signals corresponding to said received light;

at least one current source having an output connected to at least one of said LED terminals, said at least one current source supplying current to said LED through said output;

a detector connected to at least one terminal of said LED, said detector including means to sense a signal level present on the said at least one terminal of said LED to which it is connected in response to current being supplied to said LED, and said detector further including means to generate an output signal responsive to said sensed signal level; and a processor coupled to receive said output signal from said detector, said processor including means for responding to said output signal by determining variations in operating characteristics of said LED resulting from changes in the temperature of said LED and compensating for said determined variations in operating characteristics by producing signals representative of correspondingly modified output signals from said photodetector to thereby substantially eliminate the effects of said temperature changes.

11. The spectroscope as defined in claim 10 wherein said at least one current source includes a trickle current source for generating a trickle current at said current source output.

12. The spectroscope as defined in claim 11, wherein said at least one current source further includes a pulse current source generating an intermittent current pulse at said current source output.

13. The spectroscope as defined in claim 12 wherein said processor includes means for determining variations in the operating characteristics of said LED responsive to said trickle current.

14. The apparatus as defined in claim 10, where said processor includes a memory whose content includes at least one stored reference parameter which characterizes the operation of said LED.

15. The apparatus as defined in claim 14, wherein said processor includes means to determine variations in the operating characteristics of said LED based upon said at least one stored reference parameter and said detector output signal.

16. The apparatus as defined in claim 14, wherein said processor includes means to determine variations in a wavelength of light emitted from said LED as a function of said reference parameter and said detector output.

17. The apparatus as defined in claim 14, wherein said processor includes means to determine variations in the intensity of light emitted from said LED as a function of said reference parameter and said detector output.

18. A method of compensating for temperature variations of an LED used in a spectroscope, comprising the steps of:

applying a reference current to the LED;

detecting a resultant voltage at one terminal of the LED responsive to the reference current being applied to the LED and outputting a detection signal responsive thereto;

determining a variation in operating characteristics of the LED resulting from temperature variations from the detection signal ,and a stored parameter signal;

detecting a sensed spectroscopic signal using a photodetector optically coupled to the LED; and adjusting a sensed spectroscopic signal detected by the photodetector responsive to a light pulse being output by the LED based on the determined variation in operating characteristics.

19. The method as defined in claim 18 wherein the step of applying a reference signal includes applying a low level constant current.

20. The method as defined in claim 19, wherein said step of applying further includes superimposing current pulses on the low level constant current.

21. The method as defined in claim 20, wherein said step of determining a variation is performed when pulses of current are not applied to the LED.

* * * * *

UNITED STATES PATENT AND TRADEMARK OFFICE
CERTIFICATE OF CORRECTION

PATENT NO. : 5,477,853
DATED : December 26, 1995
INVENTOR(S) : Farkas et al.

It is certified that error appears in the above-indentified patent and that said Letters Patent is hereby corrected as shown below:

Column 3, line 60
    "an" should be --art--.

Column 4, line 44;
    "Fig. 3" should be --Fig. 4--.

Column 5, line 7
    After "wavelength" insert --$\lambda_c$--.

Column 6, lines 33 and 34
    "50" should be --48--.

Column 7, line 19
    After "are to" insert --be--.

Column 9, Claim 10, line 22
    "and" should be --an--.

UNITED STATES PATENT AND TRADEMARK OFFICE
CERTIFICATE OF CORRECTION

PATENT NO. : 5,477,853  
DATED : December 26, 1995  
INVENTOR(S) : Farkas et al.

Page 2 of 2

It is certified that error appears in the above-indentified patent and that said Letters Patent is hereby corrected as shown below:

Column 10, Claim 18, line 35
  ",and" should be --and--.

Signed and Sealed this

Seventeenth Day of September, 1996

Attest:

BRUCE LEHMAN

Attesting Officer

Commissioner of Patents and Trademarks